(12) United States Patent
Akagane

(10) Patent No.: US 11,490,949 B2
(45) Date of Patent: Nov. 8, 2022

(54) TREATMENT TOOL

(71) Applicant: Olympus Corporation, Hachioji (JP)

(72) Inventor: Tsunetaka Akagane, Hachioji (JP)

(73) Assignee: OLYMPUS CORPORATION, Tokyo (JP)

( * ) Notice: Subject to any disclaimer, the term of this patent is extended or adjusted under 35 U.S.C. 154(b) by 383 days.

(21) Appl. No.: 16/600,419

(22) Filed: Oct. 11, 2019

(65) Prior Publication Data
US 2020/0038088 A1 Feb. 6, 2020

Related U.S. Application Data

(63) Continuation of application No. PCT/JP2017/015440, filed on Apr. 17, 2017.

(51) Int. Cl.
*A61B 18/08* (2006.01)
*A61B 18/14* (2006.01)
*A61B 18/00* (2006.01)

(52) U.S. Cl.
CPC .......... *A61B 18/08* (2013.01); *A61B 18/1445* (2013.01); *A61B 2018/00083* (2013.01); *A61B 2018/00589* (2013.01)

(58) Field of Classification Search
CPC .............. A61B 18/08; A61B 18/1445; A61B 2018/00083; A61B 2018/00589;
(Continued)

(56) References Cited

U.S. PATENT DOCUMENTS 5,308,311 A 5/1994 Shaw
2003/0187429 A1* 10/2003 Karasawa ............ A61B 18/085
606/29

(Continued)

FOREIGN PATENT DOCUMENTS

JP S54-034284 U 3/1979
JP 7-509620 10/1995
(Continued)

OTHER PUBLICATIONS

International Search Report and Written Opinion from corresponding International Application No. PCT/JP2017/001544, dated Apr. 18, 2017.

*Primary Examiner* — Khadijeh A Vahdat
*Assistant Examiner* — Mystee Nguyen Delgado
(74) *Attorney, Agent, or Firm* — Oliff PLC

(57) ABSTRACT

The disclosed technology is directed to a treatment tool having a blade. The blade includes a treatment surface configured to engage with a treatment target. A heater is configured to be coupled to the blade. The heater includes respective first and second heat generating surfaces each of which extending in a direction transverse to the treatment surface. Respective first and second thermally conductive members each of which is interposed between the respective first and second heat generating surfaces and the blade so as to thermally engage the respective first and second heat generating surfaces and the blade to one another. The respective first and second thermally conductive members includes respective first and second thermal conductivity anisotropies each of which being higher in longitudinal directions of the blade and each of which being lower in widthwise directions of the blade that are transverse to the longitudinal directions.

19 Claims, 3 Drawing Sheets

(58) Field of Classification Search
CPC .. A61B 2018/00607; A61B 2018/1452; A61B 2090/034; A61B 18/085; A61B 2018/0063; A61B 2018/00994
See application file for complete search history.

(56) References Cited

U.S. PATENT DOCUMENTS

2005/0021017 A1    1/2005  Karasawa et al.
2011/0014417 A1*   1/2011  Lemak ................ H01L 23/4006
                                                           427/407.1

FOREIGN PATENT DOCUMENTS

| JP | 2005-040215  | 2/2005 |
| JP | 2005-261916  | 9/2005 |
| JP | 2005-1261773 | 9/2005 |
| JP | 2016-027843  | 2/2016 |

* cited by examiner

TREATMENT TOOL

CROSS-REFERENCE TO RELATED APPLICATION

This application is a continuation application of PCT Application No. PCT/JP2017/015440 filed on Apr. 17, 2017, which is hereby incorporated by reference in its entirety.

TECHNICAL FIELD

The disclosed technology relates to a treatment tool for treating a treatment target such as, for example, a biological tissue, also known as, biotissue with thermal energy.

DESCRIPTION OF THE RELATED ART

Japanese Patent Application JP 2005-261773A (PTL 1) discloses a general surgical treatment tool. The surgical treatment tool includes a heat transmitting member disposed in a gripping portion and having a heat generating body embedded therein. The surgical treatment tool can perform a treatment for incising and coagulating a biotissue by causing the heat generating body to generate heat.

BRIEF SUMMARY OF EMBODIMENTS

The disclosed technology has been made in view of the foregoing. One aspect of the disclosed technology is directed to a treatment tool includes a blade having a treatment surface configured to engage with a treatment target. A heater is configured to be coupled to the blade. The heater includes a first heat generating surface extending in a direction transverse to the treatment surface. A first thermally conductive member is interposed between the first heat generating surface and the blade so as to thermally engage the first heat generating surface and the blade to one another. The first thermally conductive member includes a first thermal conductivity anisotropy that is higher in longitudinal directions of the blade and is lower in widthwise directions of the blade that are transverse to the longitudinal directions.

Another aspect of the disclosed technology is directed to a treatment tool comprising a blade having a treatment surface configured to engage with a treatment target. A heater is configured to be coupled to the blade. The heater includes respective first and second heat generating surfaces each of which extending in a direction transverse to the treatment surface. Respective first and second thermally conductive members each of which is interposed between the respective first and second heat generating surfaces and the blade so as to thermally engage the respective first and second heat generating surfaces and the blade to one another. The respective first and second thermally conductive members includes respective first and second thermal conductivity anisotropies each of which being higher in longitudinal directions of the blade and each of which being lower in widthwise directions of the blade that are transverse to the longitudinal directions.

BRIEF DESCRIPTION OF THE DRAWINGS

The technology disclosed herein, in accordance with one or more various embodiments, is described in detail with reference to the following figures. The drawings are provided for purposes of illustration only and merely depict typical or example embodiments of the disclosed technology. These drawings are provided to facilitate the reader's understanding of the disclosed technology and shall not be considered limiting of the breadth, scope, or applicability thereof. It should be noted that for clarity and ease of illustration these drawings are not necessarily made to scale.

DETAILED DESCRIPTION OF THE EMBODIMENTS

In the following description, various embodiments of the technology will be described. For purposes of explanation, specific configurations and details are set forth in order to provide a thorough understanding of the embodiments. However, it will also be apparent to one skilled in the art that the technology disclosed herein may be practiced without the specific details. Furthermore, well-known features may be omitted or simplified in order not to obscure the embodiment being described.

The surgical treatment tool described hereinbefore may possibly cause temperature irregularities or variations in the heat transmitting member depending on the manner in which the surgical treatment tool is used to perform a treatment. While the heat transmitting member is suffering temperature variations, the surgical treatment tool is unable to have its expected treating performance delivered sufficiently. Therefore, the surgical treatment tool remains to be improved.

It is an object of the disclosed technology to provide a treatment tool that is capable of improving temperature variations of a blade thereof.

First Embodiment

Figure 1:
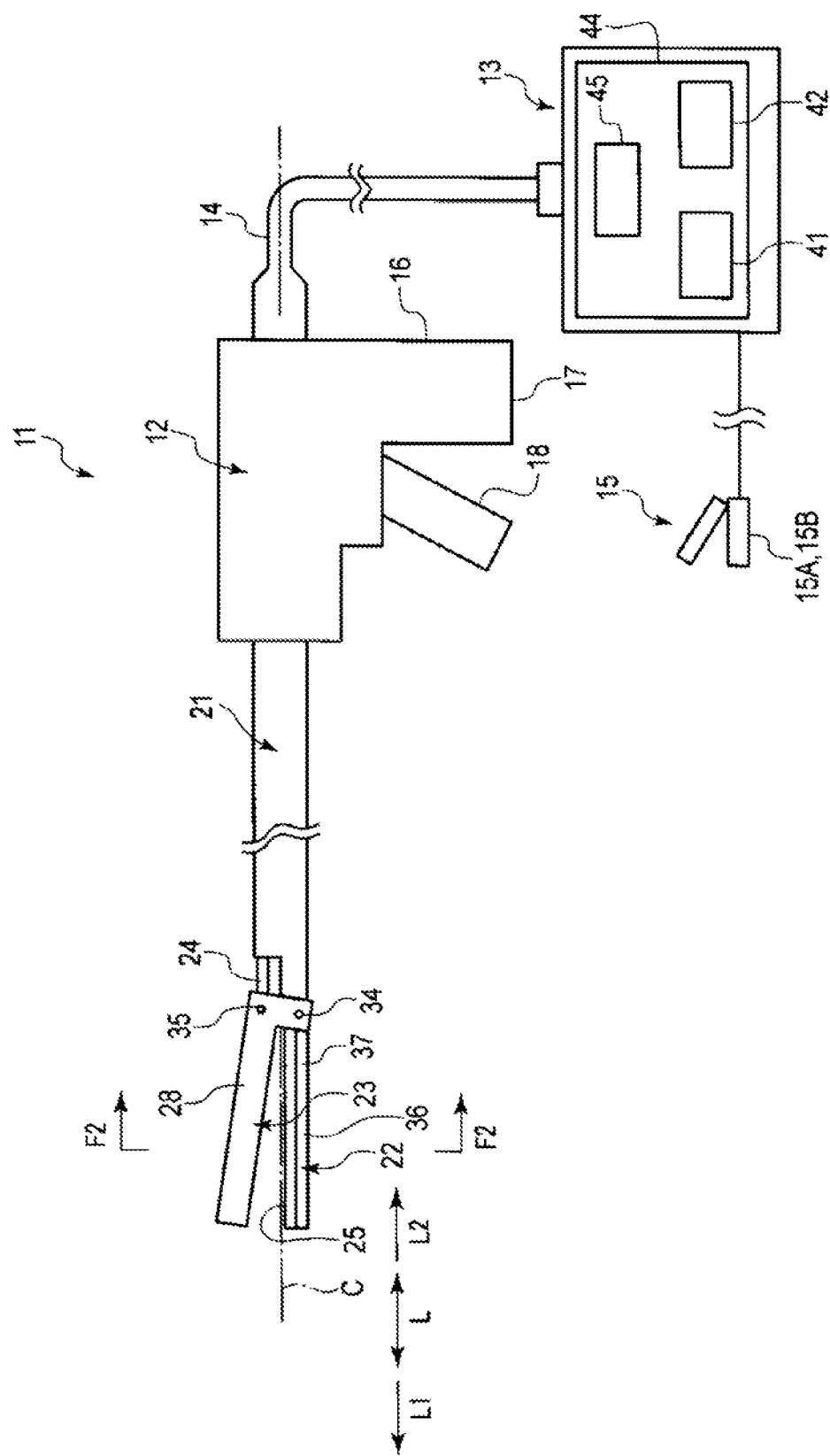
FIG. 1 is a schematic view illustrating the overall make-up of a treatment tool according to a first embodiment.

A treatment tool according to a first embodiment will be described hereinafter with reference to FIGS. 1 through 3. As illustrated in FIG. 1, a treatment tool 11, i.e., a medical device or a thermal treatment tool, includes a hand piece 12, a power supply unit 13, a cable 14 interconnecting the hand piece 12 and the power supply unit 13, and a foot switch 15, i.e., a switch, connected to the power supply unit 13 for selectively turning on and off the energy output from the power supply unit 13.

As illustrated in FIGS. 1, the hand piece 12 includes a case 16 as an outer shell, a fixed handle 17 fixedly disposed on the case 16, a movable handle 18 angularly movable with respect to the case 16, a first tubular portion 21, i.e., an outer sheath, rotatably mounted on the case 16, a first rod-shaped treatment portion 22 disposed on a distal-end side of the tubular portion 21, a second rod-shaped treatment portion 23 disposed on the distal-end side of the tubular portion 21 for engagement with and disengagement from the first treatment portion 22, and a second tubular portion 24, i.e., an inner sheath, disposed in the first tubular portion 21 and movable back and forth for angularly moving the second treatment portion 23. According to the present embodiment, one of two directions parallel to longitudinal directions L of a blade 25 is referred to as a distal-end direction L1, and the direction opposite the distal-end direction as a proximal-end direction L2. The tubular portion 21 has a central axis C. The longitudinal directions L of the blade 25 extend along the central axis C of the tubular portion 21. Directions transverse to the longitudinal directions L of the blade 25 are referred to as widthwise directions W of the blade 25. Directions extending across the blade 25 is referred to as thicknesswise directions T of the blade 25. The directions and axis thus defined will be referred to in the following description.

The surgeon operates the foot switch 15 to turn on and off the energy, i.e., thermal energy and high-frequency current energy, applied to a biotissue as a treatment target. The foot switch 15 may include a first switch 15A and a second switch 15B. The first switch 15A corresponds to a coagulation mode, for example, and outputs only high-frequency energy suitable for coagulating a biotissue and sealing a blood vessel, for example. The second switch 15B corresponds to a coagulation and incising mode, for example, and outputs thermal energy and high-frequency energy suitable for coagulating and incising a biotissue or sealing and incising a blood vessel, for example.

Figure 2:
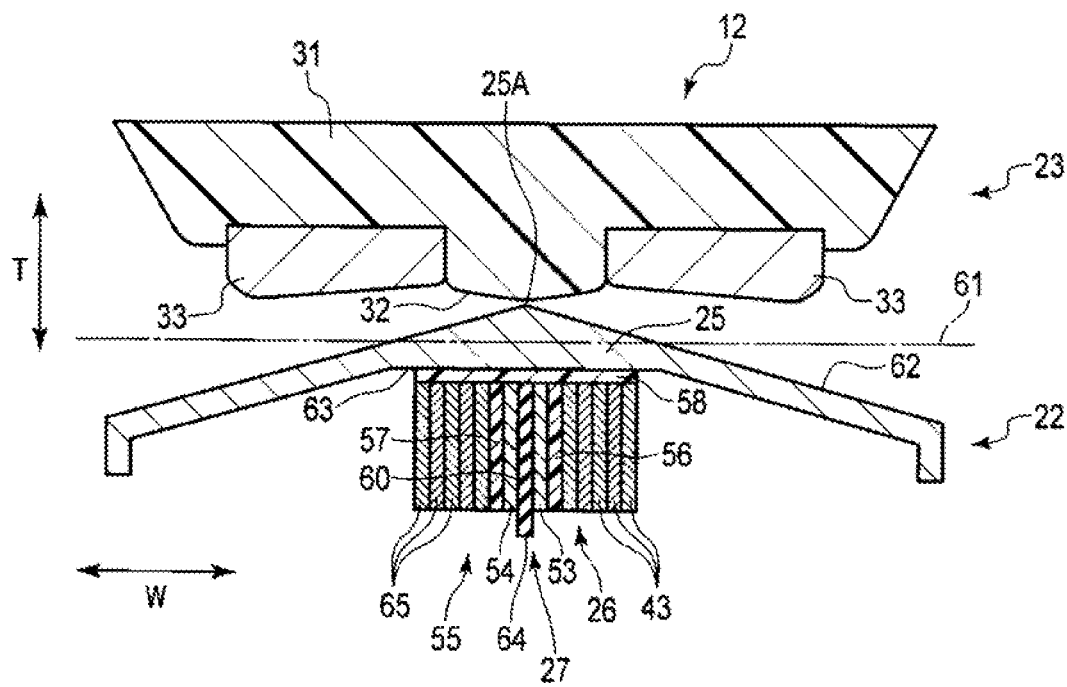
FIG. 2 is a cross-sectional view taken along line F2-F2 of FIG. 1.

As illustrated in FIGS. 1 and 2, the second treatment portion 23 has a second treatment portion body 28 made of a metal material or the like, for example, and substantially shaped as a beak, an electrode support 31 mounted on the second treatment portion body 28, an abutment portion 32 disposed on a portion of the electrode support 31, and a pair of electrodes 33 disposed one on widthwise directions W of each side of the abutment portion 32. The second treatment portion body 28 serves as an outer shell of the second treatment portion 23 and covers the side of the second treatment portion 23 that is opposite its side facing the treatment portion 22. In FIG. 2, illustration of the second treatment portion main body 28 is omitted. The electrode support 31 and the abutment portion 32 are made of a synthetic resin material, e.g., polytetrafluoroethylene (PTFE) or the like, that is heat-resistant and slippery. The abutment portion 32 protrudes toward the blade 25. The abutment portion 32 is of an arch-shaped cross section and is capable of abutting against a crest 25A of the blade 25. Each of the electrodes 33 is made of a general metal material such as copper or the like. Each of the electrodes 33 functions as one of bipolar electrodes for passing a high-frequency current through a biotissue. Each of the electrodes 33 is electrically connected to a high-frequency current supply circuit 41, to be described hereinafter, of the power supply unit 13 through an electric wire, i.e., one of first electric wires, extending through the second tubular portion 24.

The second treatment portion 23, i.e., a jaw, is angularly movably supported by a first pin 34 fixed to the distal end of the tubular portion 21. The second treatment portion 23 is angularly movable about the first pin 34 for engagement with and disengagement from the treatment portion 22. The second treatment portion 23 has a second pin 35 coupled to the distal end of the second tubular portion 24. When the user grips the movable handle 18 and turns the movable handle 18 toward the fixed handle 17, the second tubular portion 24 moves back and forth with respect to the tubular portion 21. The force with which the second tubular portion 24 moves back and forth is transmitted through the second pin 35 to the second treatment portion 23, which is opened and closed with respect to the treatment portion 22.

The treatment portion 22 has a treatment portion body 36 made of a metal material, for example, a blade 25 that serves as a portion mounted directly or indirectly on the treatment portion body 36, for contacting a biotissue, a heater 27 having a first heat generating surface 53 and a second heat generating surface 54, i.e., an opposite surface 60, a thermally conductive member 26 interposed between the heat generating surface 53 and the blade 25 to thermally connect them, a second thermally conductive member 55 interposed between the second heat generating surface 54, i.e., the opposite surface 60, and the blade 25 to thermally connect them, a first adhesive sheet 56, i.e., a film, bonding the heat generating surface 53 and the thermally conductive member 26 to each other, a second adhesive sheet 57, i.e., a second film, bonding the second heat generating surface 54, i.e., the opposite surface 60, and the second thermally conductive member 55 to each other, and a third adhesive sheet 58, i.e., a third film, bonding the blade 25 and the thermally conductive member 26 to each other and also bonding the blade 25 and the second thermally conductive member 55 to each other. The treatment portion body 36 serves as an outer shell of the treatment portion 22 and defines a rear surface 37 positioned on the side of the treatment portion 22 that is opposite the blade 25 (the treatment portion body 36 is omitted from illustration in FIG. 2). Each of the first through third adhesive sheets 56 through 58, i.e., the film, the second film, and the third film, includes a thermally conductive adhesive sheet that is insulative and highly thermally conductive.

The blade 25 serves as a portion for coagulating and incising a biotissue with heat, and doubles as an electrode, i.e., the other of the bipolar electrodes, for passing a high-frequency current through a biotissue. On the treatment tool 11 according to the present embodiment, directions along the widthwise directions W and in which a biotissue to be treated extends represent a treatment surface 61 of the blade 25. From the standpoint of preventing a biotissue from sticking to the treatment surface 61, the blade 25 in reality includes a pair of edge surfaces 62 inclined a predetermined angle to the treatment surface 61 and a crest 25A positioned between the edge surfaces 62. The blade 25 has a placement surface 63 opposite the edge surfaces 62. The placement surface 63 extends in directions along the treatment surface 61. The thermally conductive member 26 and the second thermally conductive member 55 are fixed to the placement surface 63 by the third adhesive sheet 58. Therefore, the heat generating surface 53 is thermally connected to the blade 25 through the first adhesive sheet 56, the thermally conductive member 26, and the third adhesive sheet 58. Similarly, the second heat generating surface 54, i.e., the opposite surface 60, is thermally connected to the blade 25, i.e., the placement surface 63 through the second adhesive sheet 57, the second thermally conductive member 55, and the third adhesive sheet 58. The crest 25A is an example of an edge portion. The heater 27 is disposed directly below the crest 25A.

The blade 25 is made of a metal material of good thermal conductivity and electric conductivity, such as copper, aluminum, or the like. The blade 25 is in the form of a slender plate that is of substantially the same length as the length of the treatment portion 22. The treatment portion body 36 may be integrally formed with the tubular portion 21. The blade 25 is electrically connected to the high-frequency current supply circuit 41, to be described hereinafter, of the power supply unit 13 through an electric wire, i.e., the other of the first electric wires, extending through the second tubular portion 24.

The heater 27 includes a film 64, i.e., a base, of polyimide serving as a base, for example, the heat generating surface 53 on one surface of the film 64, and the second heat generating surface 54 on the opposite surface 60 that is opposite the one surface of the film 64. The heater 27 is constructed as a sheet-like sheet heater, and is shaped as a flat plate. The heater 27, i.e., the film 64, the heat generating surface 53, and the second heat generating surface 54 extend in directions transverse to the treatment surface 61. The second heat generating surface 54 is disposed between the opposite surface 60 and the second thermally conductive member 55. The film is a mixture of resin such as PEEK and ceramic powder with high thermal conductivity such as aluminum nitride and therefore, the film is conductive as well as insulative.

Each of the heat generating surface 53 and the second heat generating surface 54 is in the form of a metal foil deposited to a predetermined pattern, i.e., a pattern of straight lines and curved lines combined together, on the one surface of the film 64. Each of the heat generating surface 53 and the second heat generating surface 54 can generate heat when it is energized as a resistor, i.e., an electric heating wire. The metal foil of each of the heat generating surface 53 and the second heat generating surface 54 should preferably be made of copper, stainless steel, or the like. The heat generating surface 53 has a pair of terminals electrically connected to a heater driving circuit 42, to be described hereinafter, of the power supply unit 13 through a pair of electric wires, i.e., second electric wires, extending through the second tubular portion 24. The second heat generating surface 54 has a pair of terminals electrically connected to the heater driving circuit 42 of the power supply unit 13 through a pair of electric wires, i.e., third electric wires, extending through the second tubular portion 24.

According to the present embodiment, the heat generating surface 53 and the second heat generating surface 54 are disposed on the both surfaces of the sheet-like heater 27. However, the second heat generating surface 54, for example, may be dispensed with. In this case, heat generated by the heat generating surface 53 is conducted to the opposite surface 60 and then conducted through the second thermally conductive member 55 to the blade 25. According to the present embodiment, furthermore, the heat generating surface 53 and the second heat generating surface 54 are individually disposed on the both surfaces of the sheet-like heater 27. However, the heat generating surface 53 and the second heat generating surface 54 may be electrically connected to each other. Specifically, a heat generating surface may be disposed on one surface of the sheet-like heater 27, i.e., the film 64, and the heater 27, i.e., the film 64, may be folded back on itself at its center such that the heat generating surface is positioned outside. One of the surfaces of the folded heater 27 may be used as the heat generating surface 53, whereas the other surface may be used as the second heat generating surface 54. With this structure, both the heat generating surface 53 and the second heat generating surface 54 can be supplied with electric power through a pair of electric wires, i.e., the second electric wires. Thus, the third electric wires can be dispensed with, resulting in a reduced number of electric wires.

The thermally conductive member 26 has a length that is substantially the same as the length of the treatment portion 22, i.e., the blade 25, along the longitudinal directions L. Stated otherwise, the thermally conductive member 26 extends over the entire length of the blade 25 along the longitudinal directions L. The thermally conductive member 26 is in the form of a slender block that extends in directions along the longitudinal directions L. The thermally conductive member 26 has such thermal conductivity anisotropy that its thermal conductivity is higher in the longitudinal directions L of the blade 25 and its thermal conductivity is lower in the widthwise directions W that are transverse to the longitudinal directions L. Furthermore, the thermally conductive member 26 also has such thermal conductivity anisotropy that its thermal conductivity is higher in the plane directions of a plane along the heat generating surface 53 and its thermal conductivity is lower in the widthwise directions W that are transverse to the longitudinal directions L.

Figure 3:
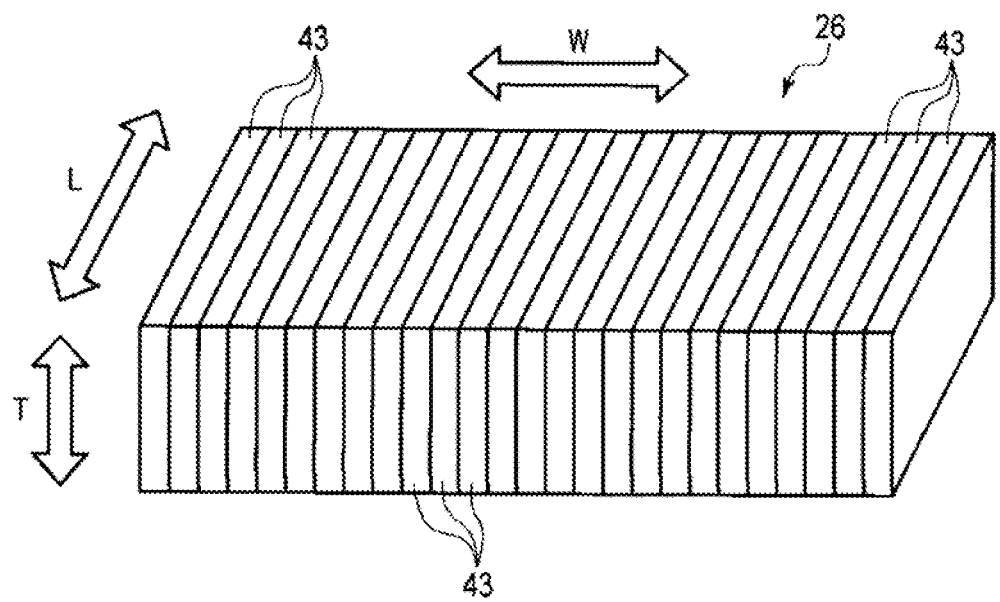
FIG. 3 is a perspective view of a thermally conductive member illustrated in FIG. 2.

As illustrated in FIGS. 2 and 3, the thermally conductive member 26 is in the form of a block including a stack of sheets 43 that are made of a material containing carbon as a main component. Each of the sheets 43 extends in the plane directions of a plane along the heat generating surface 53. Although the sheets 43 should preferably be made of graphite, they may be sheets made of a material containing another carbon as a main component, e.g., carbon fiber, carbon nanotube, or the like. The thermally conductive member 26 can be formed as a block, i.e., can be made as a unitary body, by bonding the sheets 43 or sintering the sheets 43 while keeping them in abutment together. In other words, the thermally conductive member 26 is a structural body in which the sheets 43 are integrally formed in advance. In the case where the sheets 43 are made of graphite, the thickness of each sheet 43 ranges from several to several hundreds μm, for example. In the case where the sheets 43 are made of graphite, the thermal conductivity of each sheet 43 in the plane directions thereof is of approximately 1500 W/mK, for example. The thermal conductivity of such a numerical value is much higher than the thermal conductivity of aluminum, for example, which is of approximately 200 W/mK, that is known to have good thermal conductivity. In the case where the sheets 43 are made of graphite, the thermal conductivity of each sheet 43 in a direction transverse, or perpendicular, to the plane of the sheet 43 is in a range of approximately 5 to 10 W/mK, for example, that is approximately equivalent to the corresponding thermal conductivity of synthetic resin or the like.

As illustrated in FIG. 2, the second thermally conductive member 55 is of a structure that is substantially the same as the thermally conductive member 26. The second thermally conductive member 55 is in the form of a block including a stack of second sheets 65 that are made of a material containing carbon as a main component. The second thermally conductive member 55 has such thermal conductivity anisotropy that its thermal conductivity is higher in the longitudinal directions L of the blade 25 and lower in the widthwise directions W transverse to the longitudinal directions L. The second thermally conductive member 55 also has such thermal conductivity anisotropy that its thermal conductivity is higher in the plane directions of a plane along the opposite surface 60, i.e., the second heat generating surface 54, and lower in the widthwise directions W. Each of the second sheets 65 extends in the plane directions of a plane along the opposite surface 60. Although the second sheets 65 should preferably be made of graphite, they may be sheets made of a material containing another carbon as a main component, e.g., carbon fiber, carbon nanotube, or the like. The second thermally conductive member 55 can be formed by a process that is similar to the process for forming the thermally conductive member 26. In other words, the second thermally conductive member 55 is a structural body in which the second sheets 65 are integrally formed in advance. In the case where the second sheets 65 are made of graphite, the thermal conductivity of each second sheet 65 in the plane directions thereof is of approximately 1500 W/mK, for example, and the thermal conductivity of each second sheet 65 in a direction transverse, or perpendicular, to the plane thereof is in a range of approximately 5 to 10 W/mK, for example.

As illustrated in FIG. 1, the power supply unit 13 has a controller 44. The controller 44 includes a printed circuit board and a central processing unit (CPU), a read-only memory (ROM), a random access memory (RAM), and a flash memory that are mounted on the printed circuit board. Functionally, the controller 44 has the heater driving circuit 42, the high-frequency current supply circuit 41, i.e., an electric energy supply, and a main control portion 45 for controlling the heater driving circuit 42 and the high-frequency current supply circuit 41. The main control portion 45 is able to control the supply of an electric current from the heater driving circuit 42 to the heater 27 and the supply of a high-frequency current, i.e., the electric energy, from the high-frequency current supply circuit 41. When the surgeon operates the first switch 15A of the foot switch 15, the controller 44 controls the high-frequency current supply circuit 41 to supply a high-frequency current between the blade 25 and the electrode 33. When the surgeon operates the second switch 15B of the foot switch 15, the controller 44 controls the heater driving circuit 42 to supply an electric current to the heater 27 which includes the heat generating surface 53 and the second heat generating surface 54, and also controls the high-frequency current supply circuit 41 to supply a high-frequency current between the blade 25 and the electrode 33. The heater driving circuit 42 of the controller 44 controls the temperature of the heater 27 to be constant.

Operation of the treatment tool 11 according to the present embodiment will be described hereinafter. Prior to treating a biotissue as a treatment target using the treatment tool 11 according to the present embodiment, the surgeon keeps a path or port for accessing the treatment target, using a tubular guide, such as a cannula or the like, that can pierce a patient's skin or the like.

The surgeon can sandwich the biotissue as the treatment target between the treatment portion 22, i.e., the blade 25, and the second treatment portion 23, i.e., the abutment portion 32, in a treatment target region. Furthermore, the surgeon can apply high-frequency current energy to the biotissue sandwiched between the blade 25 and the electrode 33 by operating the first switch 15A that corresponds to the coagulation mode. The applied high-frequency current energy can coagulate the biotissue and seal a blood vessel. The surgeon can also apply thermal energy and high-frequency current energy to the biotissue by operating the second switch 15B that corresponds to the coagulation and incising mode. At this time, the temperature of the heater 27 rises to a high temperature of 200° C. or higher, for example.

The thermally conductive member 26 and the second thermally conductive member 55 are of substantially the same length as the blade 25 in the longitudinal directions L. Each of the sheets 43 of the thermally conductive member 26 and each of the second sheets 65 of the second thermally conductive member 55 are highly thermally conductive in the longitudinal directions L and thicknesswise directions T which are their plane directions. Therefore, heat or thermal energy transmitted from the heat generating surface 53 and the second heat generating surface 54 of the heater 27 is spread in the longitudinal directions L by the thermally conductive member 26 and the second thermally conductive member 55, resulting in thermal equilibrium in the thermally conductive member 26 and the second thermally conductive member 55 where the temperature is uniform along the longitudinal directions L therein. With respect to the widthwise directions W, the heat transmitted from the heater 27 is slightly conducted in a direction away from the heater 27 in the thermally conductive member 26 and the second thermally conductive member 55.

The heat or thermal energy that has uniformly spread in the longitudinal directions L is also transferred to the blade 25 via the thermally conductive member 26 and the second thermally conductive member 55 that also have a high thermal conductivity in the thicknesswise directions T. The heat is thus uniformly transferred to the blade 25, making the blade 25 uniform in temperature. The temperature of the heater 27, i.e., the heat generating surface 53 and the second heat generating surface 54, that transfers the heat to the thermally conductive member 26 and the second thermally conductive member 55 is kept uniform in the longitudinal directions L by the action of the thermally conductive member 26 and the second thermally conductive member 55.

In the event that the heater 27 is suffering temperature variations, for example, when the controller 44 controls the heater driving circuit 42 to raise the temperature of the heater 27 based on the areas thereof where the temperature is lower, the areas of the heater 27 where the temperature is higher possibly tend to be overheated. The overheating may lead to damage of the heater 27. According to the present embodiment, since the temperature of the heater 27 is kept uniform in the longitudinal directions L, the heater 27 is prevented from being damaged by overheating. The treatment tool 11 thus has its reliability increased.

According to the present embodiment, while a biotissue and a blood vessel are being coagulated mainly by high-frequency current energy, the biotissue and the blood vessel are incised mainly by thermal energy transmitted to the blade 25 as described hereinbefore. In the coagulation and incising mode, therefore, the two types of energy, i.e., thermal energy and high-frequency current energy, are applied to efficiently treat, i.e., coagulate and incise, the sandwiched biotissue.

According to the first embodiment, the treatment tool 11 includes the blade 25 having the treatment surface 61 that contacts a biotissue, the heater 27 having the heat generating surface 53 extending in a direction transverse to the treatment surface 61, and the thermally conductive member 26 disposed between the heat generating surface 53 and the blade 25 in order to thermally connect them. The thermally conductive member 26 has such thermal conductivity anisotropy that its thermal conductivity is higher in the longitudinal directions L of the blade 25 and lower in the widthwise directions W that are transverse to the longitudinal directions L.

With this arrangement, the thermally conductive member 26 that has the thermal conductivity anisotropy is capable of conducting the heat conducted from the heat generating surface 53 so as to spread uniformly in the longitudinal directions L of the blade 25. Therefore, the temperature of the blade 25 is made uniform by thus conducting the heat that has uniformly spread in the longitudinal directions L to the blade 25. The heat is also prevented from wastefully spreading in the widthwise directions W of the blade 25. It is thus possible to prevent difficulties such as coagulating and incising performance variations from occurring in different areas such as the distal-end side L1 and the proximal-end side L2 of the blade 25. The treatment tool 11 can easily cut a biotissue when it incises the biotissue as heat can concentrate on a portion of the blade 25 in the widthwise directions W. In addition, the temperature of the heater 27 can be uniformized by the action of the thermally conductive member 26, preventing the heater 27 from being damaged by overheating and making the treatment tool 11 highly reliable.

The thermally conductive member 26 has such thermal conductivity anisotropy that its thermal conductivity is higher in the plane directions of a plane along the heat generating surface 53 and lower in the widthwise directions W. This arrangement can not only spread heat uniformly in the longitudinal directions L of the blade 25, but also increase the thermal conductivity in the thicknesswise directions T of the blade 25 for efficiently conducting heat from the heater 27 to the blade 25.

The thermally conductive member 26 includes a plurality of stacked sheets 43 extending in the plane directions of a plane along the heat generating surface 53. With this arrangement, the thermally conductive member 26 whose thermal conductivity is higher in the plane directions of a plane along the heat generating surface 53 can be realized by a simple structure.

Each of the sheets 43 is made of a material containing carbon as a main component. With this arrangement, since the sheets 43 of the thermally conductive member 26 are made of a material containing carbon whose thermal conductivity is good, the heat of the heater 27 can efficiently be conducted in the longitudinal directions L and the thicknesswise directions T. The temperature of the blade 25 is thus uniformized to prevent different treating performances from taking place in different areas of the blade 25 in the longitudinal directions L.

Each of the sheets 43 is made of graphite. With this arrangement, the sheets 43 of the thermally conductive member 26 are made of graphite that has an extremely good thermal conductivity and is less costly. Therefore, the treatment tool 11 whose treating performance is good and whose manufacturing cost is relatively low is realized.

The heater 27 is in the form of a flat plate. This structure makes the heater 27 low in profile, reduces a space required to install the heater 27 therein, and reduces the size of structures around the heater 27.

The treatment tool 11 includes the opposite surface 60 disposed on the side of the heater 27 that is opposite the heat generating surface 53, and the second thermally conductive member 55 interposed between the opposite surface 60 and the blade 25 to thermally connect them. The second thermally conductive member 55 has such thermal conductivity anisotropy that its thermal conductivity is higher in the longitudinal directions L and lower in the widthwise directions W.

With this arrangement, since the second thermally conductive member 55 is disposed on the opposite surface 60 in addition to the thermally conductive member 26 on the heat generating surface 53, the heat from the heater 27 can be conducted to not only the heat generating surface 53 but also the opposite surface 60. Therefore, a distribution of heat is not localized to the heat generating surface 53 side, but is also uniformly present on the opposite surface 60 side. Heat is thus distributed evenly to a certain extent not only in the longitudinal directions L but also in the widthwise directions W of the blade 25. As a consequence, it is possible to prevent difficulties such as coagulating and incising performance variations from occurring in different areas of the blade 25 in the widthwise directions W.

According to the present embodiment, the second heat generating surface 54 that extends in directions transverse to the treatment surface 61 is disposed between the opposite surface 60 and the second thermally conductive member 55. Even if no heat source is disposed on the opposite surface 60, the heat from the heat generating surface 53 is conducted through the heater to the opposite surface 60. Therefore, heat is somewhat conducted to the opposite surface 60 side though the quantity of heat conducted to the opposite surface 60 side is small compared with the heat generating surface 53 side. According to the arrangement described hereinbefore, as the heat source is disposed on the opposite surface 60 side, a distribution of heat is prevented from being localized between the heat generating surface 53 and the opposite surface 60.

The heater 27 is disposed directly below the edge portion on the blade 25. With this arrangement, the heat generated by the heater 27 is efficiently supplied to the edge portion.

Second Embodiment

A treatment tool 11 according to a second embodiment will be described hereinafter with reference to FIG. 4. The treatment tool 11 according to the second embodiment is different from the first embodiment in that the treatment portion 22 includes a third thermally conductive member 71, but has other parts in common with the first embodiment. Hereinafter, those parts that are different from the first embodiment will mainly be described, and those parts that are in common with the first embodiment will not be illustrated or described.

The third thermally conductive member 71 is in the form of a block having a U shape that is projected in a direction away from the blade 25. The third thermally conductive member 71 has substantially the same length as the length of the treatment portion 22, i.e., the blade 25, along the longitudinal directions L. Stated otherwise, the third thermally conductive member 71 extends over the entire length of the blade 25 along the longitudinal directions L. The third thermally conductive member 71 is in the form of a slender block that extends in directions along the longitudinal directions L. The third thermally conductive member 71 has a first portion 72 thermally connected to the thermally conductive member 26, a second portion 73 thermally connected to the second thermally conductive member 55, and a third portion 70 which relays between the first portion and the second portion and is integrally formed with the first portion and the second portion. The third thermally conductive member 71 is thermally connected to the thermally conductive member 26 through the first portion 72 and thermally connected to the second thermally conductive member 55 through the second portion 73.

Figure 4:
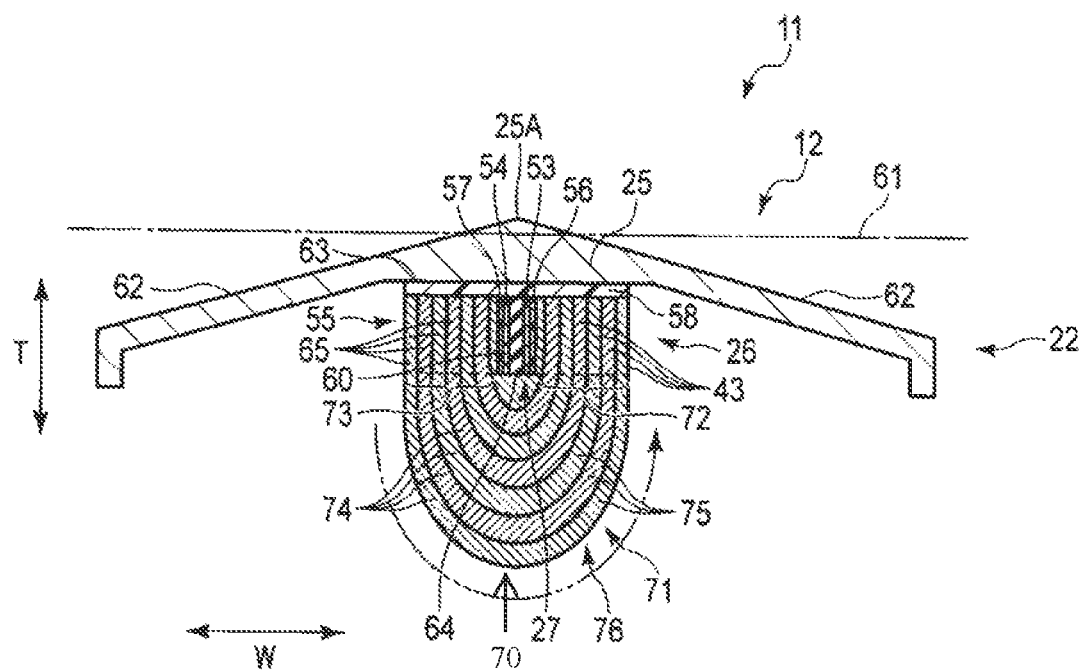
FIG. 4 is a cross-sectional view of a treatment tool according to a second embodiment, taken along a plane transverse to longitudinal directions of a blade thereof.

As illustrated in FIG. 4, the third thermally conductive member 71 is in the form of a block including a stack of third sheets 74 that are made of a material containing carbon as a main component. Each of the third sheets 74 extends in a U shape that is projected in a direction away from the blade 25 or the first portion 72 and the second portion 73. Each of the third sheets 74 should preferably be constructed as a continuous sheet 75. The continuous sheets 75 are integral with the sheets 43 of the thermally conductive member 26 on the first portion 72 side and are also integral with the second sheets 65 of the second thermally conductive member 55 on the second portion 73 side. Therefore, the third thermally conductive member 71 should preferably be formed as a portion of a unitary thermally conductive member 76 that is integrally formed with the thermally conductive member 26 and the second thermally conductive member 55. The continuous sheets 75, i.e., the third sheets 74, should preferably be made of a material containing carbon as a main component, e.g., graphite. However, the continuous sheets 75, i.e., the third sheets 74, may be sheets made of a material containing another carbon as a main component, e.g., carbon fiber, carbon nanotube, or the like.

In the case where the continuous sheets 75, i.e., the third sheets 74, are made of graphite, the thickness of each of them ranges from several to several hundreds µm, for example. In the case where the continuous sheets 75, i.e., the third sheets 74, are made of graphite, the thermal conductivity of each of them in the plane directions thereof is of approximately 1500 W/mK, for example. In the case where the continuous sheets 75, i.e., the third sheets 74, are made of graphite, the thermal conductivity of each of them in a direction transverse, or perpendicular, to the plane thereof is in a range of approximately 5 to 10 W/mK, for example, that is approximately equivalent to the corresponding thermal conductivity of synthetic resin or the like.

The unitary thermally conductive member 76 can be formed as a block, i.e., can be made as a unitary body, by bonding the continuous sheets 75 or sintering the continuous sheets 75 while keeping them in abutment together. Therefore, the third thermally conductive member 71 included in the unitary thermally conductive member 76 is a structural body in which the third sheets 74 are integrally formed in advance. Before the adhesive is dried or when the continuous sheets 75 are sintered, the continuous sheets 75 may be held in a U-shaped curved state and then bonded or sintered into the unitary thermally conductive member 76 that is of the U shape in its entirety.

The unitary thermally conductive member 76, i.e., the third thermally conductive member 71, has such thermal conductivity anisotropy that its thermal conductivity is higher along the recessed surface of its U shape that is projected in a direction away from the blade 25 and lower in a direction across the recessed surface of its U shape. Therefore, the thermal conductivity of the unitary thermally conductive member 76, i.e., the third thermally conductive member 71, is higher in both the longitudinal directions L of the blade 25 and the direction, of the thicknesswise directions T, toward the blade 25. As indicated by the two-dot-and-dash line in FIG. 4, heat directed in the direction away from the blade 25 in the unitary thermally conductive member 76, i.e., the third thermally conductive member 71, makes a U turn returning in the direction toward the blade 25 again. Therefore, the unitary thermally conductive member 76, i.e., the third thermally conductive member 71 has its thermal conductivity kept lower in the direction toward the rear surface 37.

The third thermally conductive member 71 may be formed separately from the thermally conductive member 26 and the second thermally conductive member 55. In such a case, the thermally conductive member 26 and the second thermally conductive member 55 are formed in advance as blocks according to the process described with respect to the first embodiment, and the third thermally conductive member 71 is formed as a block having a U-shaped cross section, separately from the thermally conductive member 26 and the second thermally conductive member 55. The third thermally conductive member 71 can be formed as a block, i.e., can be made as a unitary body, by bonding the third sheets 74 so as to be stacked in the thicknesswise directions or sintering the third sheets 74 while keeping them stacked together. At this time, the third thermally conductive member 71 is a structural body in which the third sheets 74 are integrally formed in advance. Before the adhesive is dried or when the third sheets 74 are sintered, the third sheets 74 may be held in a U-shaped curved state and then bonded or sintered into the third thermally conductive member 71 that is of the U-shaped cross section. Then, the thermally conductive member 26, the second thermally conductive member 55, and the third thermally conductive member 71 are bonded integrally together or further sintered integrally together while being kept in abutment together, thereby making themselves into the shape illustrated in FIG. 4.

Operation of the treatment tool 11 according to the present embodiment will be described hereinafter. According to the present embodiment, the treatment tool is brought closely to a treatment target to access the treatment target by similar process as described in the first embodiment.

The surgeon can sandwich a biotissue as the treatment target between the treatment portion 22, i.e., the blade 25, and the second treatment portion 23, i.e., the abutment portion 32, in a treatment target region. Furthermore, the surgeon can apply high-frequency current energy to the biotissue sandwiched between the blade 25 and the electrode 33 by operating the first switch 15A that corresponds to the coagulation mode, in the same manner as with the first embodiment. The applied high-frequency current energy can coagulate the biotissue and seal a blood vessel. The surgeon can also apply thermal energy and high-frequency current energy to the biotissue by operating the second switch 15B that corresponds to the coagulation and incising mode. At this time, the temperature of the heater 27 rises to a high temperature of 200° C. or higher, for example.

The unitary thermally conductive member 76 extends over substantially the entire length of the blade 25 along the longitudinal directions L. Each of the continuous sheets 75 of the unitary thermally conductive member 76 has a thermal conductivity that is higher in the longitudinal directions L as the plane directions thereof and the direction toward the blade 25 with respect to the thicknesswise directions T. On the other hand, in the direction away from the blade 25 with respect to the thicknesswise directions T, the thermal conductivity of each of the continuous sheet 75 is kept lower due to the effect of the U turn. Therefore, the heat transmitted from the heat generating surface 53 and the second heat generating surface 54 of the heater 27 is spread in the longitudinal directions L by the thermally conductive member 26 and the second thermally conductive member 55 included in the unitary thermally conductive member 76, resulting in thermal equilibrium in the thermally conductive member 26 and the second thermally conductive member 55 where the temperature is uniform along the longitudinal directions L therein. With respect to the widthwise directions W, the heat transmitted from the heater 27 is slightly conducted in the direction away from the heater 27 in the thermally conductive member 26 and the second thermally conductive member 55.

The heat that has uniformly spread in the longitudinal directions L is also transferred to the blade 25 via the thermally conductive member 26 and the second thermally conductive member 55 that also have a high thermal conductivity in the direction, of the thicknesswise directions T, toward the blade 25. At this time, since the heat transmitted from the thermally conductive member 26 and the second thermally conductive member 55 to the blade 25 does not spread significantly in the widthwise directions W, but concentrates closely on the crest 25A, it can incise the biotissue efficiently. On the other hand, the heat transmitted from the heater 27 in the direction, of the thicknesswise directions T, away from the blade 25, makes a U turn returning in the direction toward the blade 25 as indicated by the two-dot-and-dash-line arrow in FIG. 4, and is conducted to the blade 25. Therefore, the heat that is directed in the direction away from the blade 25 is less likely to be conducted toward the treatment portion body 36 side, i.e., the rear surface 37 side and to make the temperature higher on the treatment portion body 36 side, i.e., the rear surface 37 side.

Accordingly, heat is uniformly conducted to the blade 25, resulting in a uniform temperature of the blade 25 in the longitudinal directions L. Furthermore, the temperature of the heater 27, i.e., the heat generating surface 53 and the second heat generating surface 54, that conducts heat to the thermally conductive member 26 and the second thermally conductive member 55 is kept uniform with respect to the longitudinal directions L by the action of the thermally conductive member 26 and the second thermally conductive member 55. Therefore, the heater 27 is prevented from being damaged by overheating due to temperature variations on the heater 27.

According to the present embodiment, while a biotissue and a blood vessel are being coagulated mainly by high-frequency current energy, the biotissue and the blood vessel are incised mainly by thermal energy transmitted to the blade 25 as described hereinbefore. In the coagulation and incising mode, therefore, the two types of energy, i.e., thermal energy and high-frequency current energy, are applied to efficiently treat, i.e., coagulate and incise, the sandwiched biotissue.

According to the present embodiment, the treatment tool 11 includes the third thermally conductive member 71 having the first portion 72 thermally connected to the thermally conductive member 26 and the second portion 73 thermally connected to the second thermally conductive member 55, the third thermally conductive member 71 having such thermal conductivity anisotropy that its thermal conductivity is higher along the recessed surface of its U shape that is projected in the direction away from the blade 25 and lower in the direction across the recessed surface of its U shape.

With this arrangement, heat conducted from the heat generating surface 53 can be conducted so as to spread uniformly in the longitudinal directions L of the blade 25 by the thermally conductive member 26 that has thermal conductivity anisotropy. Therefore, the temperature of the blade 25 is made uniform by thus conducting the heat that has uniformly spread in the longitudinal directions L to the blade 25. The heat is also prevented from wastefully spreading in the widthwise directions W of the blade 25. It is thus possible to prevent difficulties such as coagulating and incising performance variations from occurring in different areas such as the distal-end side L1 and the proximal-end side L2 of the blade 25. In addition, the temperature of the heater 27 can be uniformized in the longitudinal directions L by the action of the thermally conductive member 26, preventing the heater 27 from being damaged by overheating and making the treatment tool 11 highly reliable.

With the arrangement described hereinbefore, moreover, the third thermally conductive member 71 is able to lower the thermal conductivity in the direction away from the blade 25 with respect to the longitudinal directions L of the blade 25. Consequently, the heat from the heater 27 is made less flowable toward the rear surface 37 opposite the blade 25. The temperature on the rear surface 37 side is thus prevented from becoming higher. The temperature of the rear surface 37 is prevented from increasing, reducing thermal invasion of other regions than the treatment target region.

The third thermally conductive member 71 includes a stack of third sheets 74 each extending in a U shape that is projected in the direction away from the blade 25. With this arrangement, the third thermally conductive member 71 having such thermal conductivity anisotropy that its thermal conductivity is higher along the recessed surface of its U shape that is projected in the direction away from the blade 25 and lower in the direction across the recessed surface of its U shape can be realized in a simple structure.

The thermally conductive member 26 includes a plurality of stacked sheets 43 each extending in the plane directions of the plane along the heat generating surface 53. The second thermally conductive member 55 includes a plurality of stacked second sheets 65 each extending in the plane directions of the plane along the opposite surface 60. Each of the third sheets 74 is integrally formed with one of the sheets 43 on the first portion 72 side and integrally formed with one of the second sheets 65 on the second portion 73 side. With this arrangement, as the sheets 43, the second sheets 65, and the third sheets 74 are integrally formed with each other, thermal conduction is not interrupted at the positions of their boundaries. Therefore, the heat directed in the direction away from the blade 25 with respect to the thicknesswise direction T can efficiently be returned to the blade 25. The thermal efficiency of the treatment tool 11 is thus increased. Since the sheets 43, the second sheets 65, and the third sheets 74 are integrally formed in advance with each other, it is not necessary to join and integrally combine the thermally conductive member 26, the second thermally conductive member 55, and the third thermally conductive member 71. Therefore, the manufacturing process is simplified.

The disclosed technology is not limited to the embodiments described hereinbefore, but changes and modifications may be made therein without departing from the scope of the invention. Furthermore, the treatment tools according to the embodiments and the modifications described hereinbefore may be combined into a single treatment tool.

In sum, one aspect of the disclosed technology is directed to a treatment tool includes a blade having a treatment surface configured to engage with a treatment target. A heater is configured to be coupled to the blade. The heater includes a first heat generating surface extending in a direction transverse to the treatment surface. A first thermally conductive member is interposed between the first heat generating surface and the blade so as to thermally engage the first heat generating surface and the blade to one another. The first thermally conductive member includes a first thermal conductivity anisotropy that is higher in longitudinal directions of the blade and is lower in widthwise directions of the blade that are transverse to the longitudinal directions.

The first thermal conductivity anisotropy is higher in plane directions of a plane along the heat generating surface and is lower in the widthwise directions. The treatment tool further includes a first film configured to be thermally engaged to the first thermally conductive member and the heat generating surface. The first film is thermally conductive and insulative so as to join the first thermally conductive member and the first heat generating surface to one another. The first thermally conductive member is defined by a plurality of first stacked sheets extending in the plane directions of the plane along the first heat generating surface. Each of the plurality of first stacked sheets is substantially made of either carbon or graphite or combination thereof. The plurality of first stacked sheets forms an integral structural body. The heater is formed into a flat plate shape and includes a second heat generating surface that is opposite to the first heat generating surface.

A second thermally conductive member is interposed between the second heat generating surface and the blade so as to thermally engage the second heat generating surface and the blade to one another. The second thermally conductive member includes a second thermal conductivity anisotropy being higher in the longitudinal directions and being lower in the widthwise directions. The second thermal conductivity anisotropy is higher in plane directions of a plane along the opposite surface and is lower in the widthwise directions. The treatment tool further comprises a second film configured to be thermally connected to the second thermally conductive member and the second heat generating surface. The second film is thermally conductive and insulative so as to join the second thermally conductive member and the second heat generating surface to one another. The second thermally conductive member is defined by a plurality of second stacked sheets integrally formed with one another and extending in the plane directions of the plane along the opposite surface. The plurality of second stacked sheets is substantially made of either carbon or graphite or combination thereof. The heater is disposed directly below an edge portion of the blade.

The treatment tool further comprises a third thermally conductive member having respective first and second portions. The first portion is thermally connected to the first thermally conductive member and the second portion is thermally connected to the second thermally conductive member. The third thermally conductive member includes a third thermal conductivity anisotropy being higher along a recessed surface of a U shape that is projected in a direction away from the blade and being lower in a direction across the recessed surface of the U shape. The third thermally conductive member includes a plurality of third stacked sheets extending in the U shape projected in the direction away from the blade. The first thermally conductive member is defined by a plurality of first stacked sheets extending in plane directions of a plane along the first heat generating surface. The second thermally conductive member is defined by a plurality of second stacked sheets extending in plane directions of a plane along the second heat generating surface. The third stacked sheets is integrally formed with the first stacked sheets on a first portion side and integrally formed with the second stacked sheets on a second portion side. The third thermally conductive member forms an integral structural. The treatment tool further comprises an electric energy supply for supplying electric energy to the blade. The blade is made of an electrically conductive material for treating the treatment target with thermal energy supplied from the heater and the electric energy supplied from the electric energy supply. The treatment target is a biological tissue, also known as, a biotissue.

Another aspect of the disclosed technology is directed to a treatment tool comprising a blade having a treatment surface configured to engage with a treatment target. A heater is configured to be coupled to the blade. The heater includes respective first and second heat generating surfaces each of which extending in a direction transverse to the treatment surface. Respective first and second thermally conductive members each of which is interposed between the respective first and second heat generating surfaces and the blade so as to thermally engage the respective first and second heat generating surfaces and the blade to one another. The respective first and second thermally conductive members includes respective first and second thermal conductivity anisotropies each of which being higher in longitudinal directions of the blade and each of which being lower in widthwise directions of the blade that are transverse to the longitudinal directions.

While various embodiments of the disclosed technology have been described above, it should be understood that they have been presented by way of example only, and not of limitation. Likewise, the various diagrams may depict an example schematic or other configuration for the disclosed technology, which is done to aid in understanding the features and functionality that can be included in the disclosed technology. The disclosed technology is not restricted to the illustrated example schematic or configurations, but the desired features can be implemented using a variety of alternative illustrations and configurations. Indeed, it will be apparent to one of skill in the art how alternative functional, logical or physical locations and configurations can be implemented to implement the desired features of the technology disclosed herein.

Although the disclosed technology is described above in terms of various exemplary embodiments and implementations, it should be understood that the various features, aspects and functionality described in one or more of the individual embodiments are not limited in their applicability to the particular embodiment with which they are described, but instead can be applied, alone or in various combinations, to one or more of the other embodiments of the disclosed technology, whether or not such embodiments are described and whether or not such features are presented as being a part of a described embodiment. Thus, the breadth and scope of the technology disclosed herein should not be limited by any of the above-described exemplary embodiments.

Terms and phrases used in this document, and variations thereof, unless otherwise expressly stated, should be construed as open ended as opposed to limiting. As examples of the foregoing: the term "including" should be read as meaning "including, without limitation" or the like; the term "example" is used to provide exemplary instances of the item in discussion, not an exhaustive or limiting list thereof; the terms "a" or "an" should be read as meaning "at least one," "one or more" or the like; and adjectives such as "conventional," "traditional," "normal," "standard," "known" and terms of similar meaning should not be construed as limiting the item described to a given time period or to an item available as of a given time, but instead should be read to encompass conventional, traditional, normal, or standard technologies that may be available or known now or at any time in the future. Likewise, where this document refers to technologies that would be apparent or known to one of ordinary skill in the art, such technologies encompass those apparent or known to the skilled artisan now or at any time in the future.

The presence of broadening words and phrases such as "one or more," "at least," "but not limited to" or other like phrases in some instances shall not be read to mean that the narrower case is intended or required in instances where such broadening phrases may be absent.

Additionally, the various embodiments set forth herein are described in terms of exemplary schematics, block diagrams, and other illustrations. As will become apparent to one of ordinary skill in the art after reading this document, the illustrated embodiments and their various alternatives can be implemented without confinement to the illustrated examples. For example, block diagrams and their accompanying description should not be construed as mandating a particular configuration.

What is claimed is:
1. A treatment tool comprising:
 a blade having a treatment surface configured to engage with a treatment target;
 a heater configured to be coupled to the blade, the heater including:

a first heat generating surface extending in a direction transverse to the treatment surface; and
a second heat generating surface that is opposite to the first heat generating surface; and
a unitary thermally conductive member that comprises:
a first thermally conductive member being interposed between the first heat generating surface and the blade so as to thermally engage the first heat generating surface to the blade, the first thermally conductive member including a first thermal conductivity being higher in longitudinal directions of the blade and being lower in widthwise directions of the blade that are transverse to the longitudinal directions;
a second thermally conductive member interposed between the second heat generating surface and the blade so as to thermally engage the second heat generating surface to the blade; and
a third thermally conductive member that is thermally connected to the first thermally conductive member and the second thermally conductive member, the third thermally conductive member being in the form of a block having a U shape projecting in a direction away from the blade,
wherein the thermal conductivity of the unitary thermally conductive member is higher along a recessed surface of the U shape and is lower in a direction across the recessed surface of the U shape.

2. The treatment tool of claim 1, wherein
the first thermal conductivity is higher in plane directions of a plane along the first heat generating surface and is lower in the widthwise directions.

3. The treatment tool of claim 2, wherein
the first thermally conductive member is defined by a plurality of first stacked sheets extending in the plane directions of the plane along the first heat generating surface.

4. The treatment tool of claim 3, wherein
each of the plurality of first stacked sheets is substantially made of either carbon or graphite or combination thereof.

5. The treatment tool of claim 3, wherein
the plurality of first stacked sheets forms an integral structural body.

6. The treatment tool of claim 1, further comprising a first film configured to be thermally engaged to the first thermally conductive member and the first heat generating surface, and wherein the first film is thermally conductive and insulative so as to join the first thermally conductive member to the first heat generating surface.

7. The treatment tool of claim 1, wherein
the heater is formed into a flat plate shape.

8. The treatment tool of claim 1, wherein:
the second thermally conductive member includes a second thermal conductivity being higher in the longitudinal directions and being lower in the widthwise directions.

9. The treatment tool of claim 8, wherein
the second thermal conductivity is higher in plane directions of a plane along the second heat generating surface and is lower in the widthwise directions.

10. The treatment tool of claim 9, wherein
the second thermally conductive member is defined by a plurality of second stacked sheets integrally formed with one another and extending in the plane directions of the plane along the second heat generating surface, and
the plurality of second stacked sheets is substantially made of either carbon or graphite or combination thereof.

11. The treatment tool of claim 8, wherein
the heater is disposed directly below an edge portion of the blade.

12. The treatment tool of claim 1, further comprising a second film configured to be thermally connected to the second thermally conductive member and the second heat generating surface and wherein the second film is thermally conductive and insulative so as to join the second thermally conductive member to the second heat generating surface.

13. The treatment tool of claim 1, wherein
the third thermally conductive member includes a plurality of third stacked sheets extending in the U shape projected in the direction away from the blade.

14. The treatment tool of claim 13, wherein:
the first thermally conductive member includes a plurality of first stacked sheets extending in plane directions of a plane along the first heat generating surface;
the second thermally conductive member includes second stacked sheets extending in plane directions of a plane along the second heat generating surface; and
the third thermally conductive member is integrally formed with the first thermally conductive member and the second thermally conductive member.

15. The treatment tool of claim 13, wherein
the unitary thermally conductive member forms an integral structural body.

16. The treatment tool of claim 1, further comprising:
an electric energy supply for supplying electric energy to the blade,
wherein the blade is made of an electrically conductive material, for treating the treatment target with thermal energy supplied from the heater and the electric energy supplied from the electric energy supply.

17. The treatment tool of claim 1, wherein the treatment target is a biotissue.

18. A treatment tool comprising:
a blade having a treatment surface configured to engage with a treatment target;
a heater configured to be coupled to the blade, the heater includes respective first and second heat generating surfaces each of which extend in a direction transverse to the treatment surface; and
a unitary thermally conductive member which is interposed between the first and second heat generating surfaces and the blade so as to thermally engage the first and second heat generating surfaces to the blade, the unitary thermally conductive member including a thermal conductivity which is higher in longitudinal directions of the blade and which is lower in widthwise directions of the blade that are transverse to the longitudinal directions,
wherein the thermal conductivity of the unitary thermally conductive member is higher along a recessed surface of a U shape projecting in a direction away from the blade and is lower in a direction across the recessed surface of the U shape.

19. A treatment tool comprising:
a blade having a treatment surface configured to engage with a treatment target;
a heater configured to be coupled to the blade, the heater including:
a first heat generating surface extending in a direction transverse to the treatment surface; and a second heat generating surface that is opposite to the first heat generating surface; and a thermally conductive member being interposed between the first heat generating surface and the blade so as to thermally engage the first heat generating surface to the blade, the thermally conductive member including a thermal conductivity being higher in longitudinal directions of the blade and being lower in widthwise directions of the blade that are transverse to the longitudinal directions, wherein:

the thermally conductive member is thermally connected to the first heat generating surface and the second heat generating surface, and includes:
- a first portion extending in plane directions of a plane along the first heat generating surface;
- a second portion extending in plane directions of a plane along the second heat generating surface; and
- a third portion which relays between the first potion and the second portion and is integrally formed with the first portion and the second portion, the third portion being in the form of a block having a U shape projecting in a direction away from the blade, and the thermal conductivity of the thermally conductive member is higher along a recessed surface of the U shape and is lower in a direction across the recessed surface of the U shape.

* * * * *